United States Patent [19]

Keith et al.

[11] 4,432,965

[45] Feb. 21, 1984

[54] QUINIDINE SUSTAINED RELEASE DOSAGE FORMULATION

[75] Inventors: Alec D. Keith, Miami; Charles Hsiao, Cooper City, both of Fla.

[73] Assignee: Key Pharmaceuticals, Inc., Miami, Fla.

[21] Appl. No.: 396,668

[22] Filed: Jul. 9, 1982

[51] Int. Cl.$^3$ .................. A61K 9/22; A61K 9/24; A61K 9/32
[52] U.S. Cl. ..................... 424/19; 424/21; 424/32; 424/33
[58] Field of Search ................ 424/19, 22, 32, 33

[56] References Cited

U.S. PATENT DOCUMENTS

| | | | |
|---|---|---|---|
| 2,693,438 | 11/1954 | Ward | 424/33 |
| 3,096,248 | 7/1963 | Rudzki | 424/32 |
| 3,935,326 | 1/1976 | Groppenbacher et al. | 424/33 |
| 3,951,821 | 4/1976 | Davidson | 424/15 |
| 4,060,598 | 11/1977 | Groppenbacher et al. | 424/33 |
| 4,235,870 | 11/1980 | Leslie | 424/35 |
| 4,249,531 | 2/1981 | Heller et al. | 424/33 |
| 4,330,338 | 5/1982 | Banker | 424/33 |

FOREIGN PATENT DOCUMENTS

| | | | |
|---|---|---|---|
| 2363853 | 7/1975 | Fed. Rep. of Germany | 424/33 |
| 45-1274 | 1/1970 | Japan | 424/32 |
| 54-28812 | 3/1979 | Japan . | |
| 55-49312 | 4/1980 | Japan . | |
| 56-110612 | 9/1981 | Japan . . | |
| 1213348 | 11/1970 | United Kingdom | 424/32 |

*Primary Examiner*—Shep K. Rose
*Attorney, Agent, or Firm*—Wegner & Bretschneider

[57] ABSTRACT

A sustained release oral dosage form is provided comprising a tablet core containing a pharmaceutically effective amount of quinidine. The tablet core is coated with a sustained release polymeric coating which contains about 5 to about 20 percent by weight polyethylene glycol component having a molecular weight of from about 500 to about 200, and from about 80 to 95 percent by weight polyvinylalcohol component. The polyvinylalcohol component comprises from about one to about ten parts by weight of a partially hydrolyzed polyvinylalcohol subcomponent having a degree of hydrolysis of from about 75 to about 92 percent and about one part by weight of a substantially completely hydrolyzed polyvinylalcohol subcomponent having a degree of hydrolysis in excess of 95%.

4 Claims, No Drawings

QUINIDINE SUSTAINED RELEASE DOSAGE FORMULATION

SUMMARY OF THE INVENTION

Quinidine is a well known alkaloid used in the treatment of certain cardiac arrhythmias. It is a general cardiac depressant, which reduces myocardial excitability, automaticity and conductivity.

In accordance with the invention, there is provided a sustained release oral dosage form which provides a patient with quinidine over a prolonged period of time. The dosage form comprises a tablet core containing a pharmaceutically effective amount of quinidine. The tablet core is coated with a sustained release polymeric coating which contains from about 5 to about 20 percent by weight polyethylene glycol component having a molecular weight of from about 500 to about 2000, and from about 80 to about 95 percent by weight polyvinylalcohol component.

The polyvinylalcohol component comprises from about one to about ten parts by weight of a partially hydrolyzed polyvinylalcohol subcomponent, with a degree of hydrolysis of about 75 to about 92 percent molecular weight of from about 50,000 to about 110,000; and about one part by weight of a substantially completely hydrolyzed polyvinylalcohol subcomponent having a degree of hydrolysis in excess of 95% molecular weight of from about 90,000 to about 150,000.

DETAILED DESCRIPTION OF THE INVENTION

The invention provides a sustained release formulation with an increased residency time in the gastrointestinal tract, and one where the rate of partial or total dissolution of the sustained release polymeric coating can be controlled through adjustment of the ratio of the polyvinylalcohol subcomponents. In a comparison to components with a lower ratio of the partially hydrolyzed to substantially completely hydrolyzed polyvinylalcohol, the sustained release dosage form with a higher ratio will move more slowly through the gastrointestinal tract during the period of structural integrity of the sustained release polymeric coating. However, the period of structural integrity will be relatively short. Conversely, with a ratio approaching an even mixture of the two subcomponents, the structural integrity will be maintained for a longer period of time, but with a faster passage of the sustained release dosage form through the gastrointestinal tract.

In accordance with a preferred aspect of the invention, a ratio of from about 6:1 to about 2:1 of the partially hydrolyzed to substantially completely hydrolyzed components is contemplated, with a more preferred aspect of the invention providing said ratio as about 4:1.

The tablet core in a generic aspect of the invention may include a conventional tablet that is coated with the sustained release polymeric coating of the invention. In accordance with a preferred aspect of the invention, the tablet core is made of compressed granules each having a mesh size smaller than about 12 mesh, the granules being made of, for example, methylcellulose and lactose containing the quinidine.

Quinidine is defined to include any of the pharmaceutically acceptable forms of quinidine, with quinidine bisulfate as a preferred embodiment.

The sustained release polymeric coating is preferably applied through an air suspension coating technique (e.g., a six inch Wurster column manufactured by Glatt Air Techniques is satisfactory for the invention). The tablet cores are suspended in the air suspension column and coated with a spray of the polymeric mixture comprising the sustained release polymeric coating.

The total amount of quinidine should, when quinidine bisulfate is used as the form of quinidine, comprise from about 100 to about 400 mg per finished oral sustained release dosage form, with about 300 mg being contemplated in one embodiment.

The prolonged period of time will vary based upon the ratio of the polyvinylalcohol subcomponents. In accordance with a preferred aspect of the invention, a sustained release for a period of at least about 8 hours is contemplated, and in a still more preferred embodiment a release over a period of 12 hours. With a sustained release over a period of 12 hours, taking into account the half-life of the drug, the patient is provided with systemic activity at a suitable rate for a period of at least about 24 hours.

The following example illustrates the invention:

900 gm quinidine bisulfate, 300 gm of methyl cellulose (Methocel E-50, Dow) and 600 gm lactose are mixed together and granulated with 60 ml of a 2% solution of Methocel R-50. The granulation was tray-dried in a 50° C. oven for a period of 16 hours and passed through a 12 mesh screen. The resulting granulation mixture is admixed with one percent magnesium stearate and compressed into 610 mg tablet cores, each of the cores containing 300 mg quinidine bisulfate. 1000 gm of the the tablet cores are placed in a six inch Wurster air suspension coating column and a fluidized bed of the granulation mixture is created through conventional air suspension technique. While so suspended in the fluidized bed, a coating mixture of 1400 ml of a polyvinylalcohol solution which contains 54.2 gm of polyvinylalcohol, mw 76,000, 88% hydrolyzed (Mowiol 18-88, Hoechst), and 13.60 gm polyvinylalcohol, mw 115,000, 100% hydrolyzed is introduced. The process utilized at inlet air temperature of 70° C., a spray pressure of 2 bars and a liquid feed of 15 ml/min.

The resultant product was tested according to USP XX dissolution procedure, i.e., one hour in simulated gastric fluid, then is simulated intestinal fluid, with the oral sustained release dosage form showing release of quinidine bisulfate in the following order:

| Time (hrs.) | Percent release |
| --- | --- |
| 1 | 9.9 |
| 2 | 19.6 |
| 4 | 37.3 |
| 6 | 58.6 |
| 8 | 79.8 |
| 10 | 92.4 |
| 12 | 100.0 |

What is claimed is:

1. A sustained release oral dosage form for providing a patient with quinidine over a prolonged period of time which comprises a tablet core containing a pharmaceutically effective amount of quinidine, said tablet core coated with a sustained release polymeric coating which contains from about 5 to about 20 percent by weight polyethylene glycol component having a molecular weight of from about 500 to about 2000, and from about 80 to about 95 percent by weight polyvinylalcohol component comprising:
(a) about one to about ten parts by weight of a partially hydrolyzed polyvinylalcohol subcomponent molecular weight of from about 50,000 to about 110,000 having a degree of hydrolysis of about 75 to about 92 percent; and
(b) about one part by weight of a substantially completely hydrolyzed polyvinylalcohol subcomponent molecular weight of from about 90,000 to about 150,000 having a degree of hydrolysis in excess of 95%.

2. A sustained release oral dosage form of claim 1, wherein said quinidine is in the form of quinidine bisulfate.

3. A sustained release oral dosage form of claim 1, wherein said sustained release polymeric coating comprises from about three to about seven percent by weight thereof.

4. A sustained release oral dosage form of claim 1, wherein said tablet core comprises methylcellulose and lactose granules smaller than about 12 mesh which have been compressed into tablet core.

* * * * *